(12) United States Patent
Kwok et al.

(10) Patent No.: US 8,636,006 B2
(45) Date of Patent: Jan. 28, 2014

(54) MASK

(75) Inventors: Philip Rodney Kwok, Chatswood (AU); Robert Edward Styles, Glenhaven (AU)

(73) Assignee: ResMed Limited, Bella Vista (AU)

( * ) Notice: Subject to any disclaimer, the term of this patent is extended or adjusted under 35 U.S.C. 154(b) by 1654 days.

(21) Appl. No.: 11/648,537

(22) Filed: Jan. 3, 2007

(65) Prior Publication Data

US 2007/0107735 A1    May 17, 2007

Related U.S. Application Data

(63) Continuation of application No. 10/068,963, filed on Feb. 11, 2002, now Pat. No. 7,178,527, which is a continuation of application No. 09/230,491, filed as application No. PCT/AU97/00450 on Jul. 16, 1997, now Pat. No. 6,357,441.

(30) Foreign Application Priority Data

Jul. 26, 1996 (AU) ........................................ PO1265

(51) Int. Cl.
A61M 16/06    (2006.01)

(52) U.S. Cl.
USPC ............ 128/207.13; 128/206.24; 128/206.21; 128/205.25; 128/200.24

(58) Field of Classification Search
USPC .......... 128/200.24, 857, 858, 200.25, 206.21, 128/206.23, 206.24
See application file for complete search history.

(56) References Cited

U.S. PATENT DOCUMENTS

| | | | |
|---|---|---|---|
| 781,516 | A | 1/1905 | Guthrie |
| 812,706 | A | 2/1906 | Warbasse |
| 902,961 | A | 11/1908 | Goodnow |
| 1,000,706 | A | 8/1911 | Barnum |
| 1,081,745 | A | 12/1913 | Johnston at al. |
| 1,105,127 | A | 7/1914 | Drager |
| 1,192,186 | A | 7/1916 | Greene |
| 1,206,045 | A | 11/1916 | Smith |
| 1,632,449 | A | 6/1927 | McKESSON |
| 1,653,572 | A | 12/1927 | Jackson |

(Continued)

FOREIGN PATENT DOCUMENTS

| | | |
|---|---|---|
| AU | 64058/86 | 4/1987 |
| AU | 91/77110 B | 11/1991 |

(Continued)

OTHER PUBLICATIONS

Decision on Appeal (and English translation) completed Mar. 25, 2008 for corresponding Japanese Application No. 2005-23339, 21 pages.

(Continued)

*Primary Examiner* — Annette Dixon
(74) *Attorney, Agent, or Firm* — Nixon & Vanderhye P.C.

(57) ABSTRACT

A mask for use with the administration of CPAP therapy includes a mask body for connection with a supply of breathable gas pressurized above ambient; and a compliant patient contacting element including a multilayered cushioning interface. The interface has an interior layer and an exterior layer provided in spaced relation to the interior layer when the mask is not in use. The exterior layer is elastically and resiliently movable towards and away the interior layer in use. Only the exterior layer forms a contacting seal with the patient in use.

30 Claims, 3 Drawing Sheets

(56) References Cited

U.S. PATENT DOCUMENTS

| | | | |
|---|---|---|---|
| 1,926,027 A | 9/1933 | Biggs | |
| 2,123,353 A | 7/1938 | Catt | |
| 2,166,164 A | 7/1939 | Lemberg | |
| 2,248,477 A | 7/1941 | Lombard | |
| 2,254,854 A | 9/1941 | O'Connell | |
| 2,317,608 A | 4/1943 | Heidbrink | |
| 2,371,965 A | 3/1945 | Lehmberg | |
| 2,376,871 A | 5/1945 | Fink | |
| 2,415,846 A | 2/1947 | Randall | |
| 2,438,058 A | 3/1948 | Kinchaloe | |
| 2,465,973 A | 3/1949 | Bulbulian | |
| 2,578,621 A | 12/1951 | Yant | |
| 2,625,155 A | 1/1953 | Engelder | |
| 2,875,757 A | 1/1954 | Galleher, Jr. | |
| 2,931,356 A * | 4/1960 | Schwarz | 128/206.24 |
| D188,084 S | 5/1960 | Garelick | |
| 2,939,458 A | 6/1960 | Lundquist | |
| 3,013,556 A | 12/1961 | Gallaher | |
| 3,044,464 A | 7/1962 | Gray | |
| 3,182,659 A | 5/1965 | Blount et al. | |
| 3,189,027 A | 6/1965 | Bartlett | |
| 3,193,624 A | 7/1965 | Webb et al. | |
| 3,227,159 A | 1/1966 | Borgia et al. | |
| 3,238,943 A | 3/1966 | Holley | |
| 3,315,674 A | 4/1967 | Bloom, at al. | |
| 3,330,273 A * | 7/1967 | Ray | 128/206.26 |
| 3,330,274 A | 7/1967 | Bennett | |
| 3,362,420 A | 1/1968 | Blackburn et al. | |
| 3,363,833 A | 1/1968 | Laerdal | |
| 3,521,630 A | 7/1970 | Westberg et al. | |
| 3,556,122 A | 1/1971 | Laerdal | |
| 3,580,051 A | 5/1971 | Blevins | |
| 3,680,555 A | 8/1972 | Warncke | |
| 3,700,000 A | 10/1972 | Hesse et al. | |
| 3,720,235 A | 3/1973 | Schrock | |
| 3,725,953 A | 4/1973 | Johnson et al. | |
| 3,796,216 A | 3/1974 | Schwarz | |
| 3,799,164 A | 3/1974 | Rollins | |
| D231,803 S | 6/1974 | Huddy | |
| 4,015,598 A * | 4/1977 | Brown | 128/205.25 |
| 4,077,404 A | 3/1978 | Elam | |
| D250,131 S | 10/1978 | Lewis et al. | |
| 4,167,185 A | 9/1979 | Lewis | |
| 4,174,710 A | 11/1979 | Pampuch | |
| 4,226,234 A | 10/1980 | Gunderson | |
| 4,245,632 A | 1/1981 | Houston | |
| D262,322 S | 12/1981 | Mizerak | |
| 4,304,229 A | 12/1981 | Curtin | |
| 4,305,387 A | 12/1981 | Reist-Kündig et al. | |
| 4,328,797 A | 5/1982 | Rollins et al. | |
| 4,347,205 A | 8/1982 | Stewart | |
| 4,354,488 A | 10/1982 | Bartos | |
| 4,402,316 A | 9/1983 | Gadberry | |
| 4,412,537 A | 11/1983 | Tiger | |
| 4,414,973 A | 11/1983 | Matheson et al. | |
| 4,454,880 A | 6/1984 | Muto et al. | |
| 4,467,799 A | 8/1984 | Steinberg | |
| 4,522,639 A | 6/1985 | Ansite et al. | |
| 4,558,710 A | 12/1985 | Eichler | |
| 4,574,799 A | 3/1986 | Warncke | |
| 4,616,647 A | 10/1986 | McCreadie | |
| 4,622,964 A | 11/1986 | Flynn | |
| 4,655,213 A | 4/1987 | Rapoport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| H397 H | 1/1988 | Stark | |
| D293,613 S | 1/1988 | Wingler | |
| 4,739,755 A | 4/1988 | White et al. | |
| 4,770,169 A | 9/1988 | Schmoegner et al. | |
| 4,774,941 A | 10/1988 | Cook | |
| 4,782,832 A | 11/1988 | Trimble et al. | |
| 4,794,921 A | 1/1989 | Lindkvist | |
| 4,799,477 A | 1/1989 | Lewis | |
| 4,803,981 A | 2/1989 | Vickery | |
| 4,809,692 A | 3/1989 | Nowacki et al. | |
| 4,811,730 A | 3/1989 | Milano | |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Bellm | |
| 4,848,366 A | 7/1989 | Aita et al. | |
| 4,907,584 A | 3/1990 | McGinnis | |
| 4,910,806 A | 3/1990 | Baker et al. | |
| 4,919,128 A | 4/1990 | Kopala et al. | |
| 4,922,921 A | 5/1990 | Donoghue | |
| 4,938,210 A | 7/1990 | Shene | |
| 4,938,212 A | 7/1990 | Gnook et al. | |
| 4,944,310 A | 7/1990 | Sullivan | |
| D310,431 S | 9/1990 | Bellm | |
| 4,971,051 A * | 11/1990 | Toffolon | 128/206.26 |
| 4,986,269 A | 1/1991 | Hakkinen | |
| 4,989,596 A | 2/1991 | Macris et al. | |
| 4,989,599 A | 2/1991 | Carter | |
| 5,003,633 A | 4/1991 | Itoh | |
| 5,005,568 A | 4/1991 | Loescher et al. | |
| 5,005,571 A | 4/1991 | Dietz | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,063,922 A | 11/1991 | Hakkinen | |
| 5,065,756 A | 11/1991 | Rapoport | |
| 5,069,205 A | 12/1991 | Urso | |
| D323,908 S | 2/1992 | Hollister et al. | |
| 5,109,839 A | 5/1992 | Blasdell et al. | |
| 5,109,840 A | 5/1992 | Daleiden | |
| 5,121,745 A | 6/1992 | Israel | |
| 5,133,347 A | 7/1992 | Huennebeck | |
| 5,140,980 A | 8/1992 | Haughey et al. | |
| 5,140,982 A | 8/1992 | Bauman | |
| 5,148,802 A | 9/1992 | Sanders et al. | |
| 5,159,938 A | 11/1992 | Laughlin | |
| 5,178,138 A | 1/1993 | Walstrom et al. | |
| D334,633 S | 4/1993 | Rudolph | |
| 5,220,699 A | 6/1993 | Farris | |
| 5,231,983 A | 8/1993 | Matson et al. | |
| 5,233,978 A | 8/1993 | Callaway | |
| 5,243,971 A | 9/1993 | Sullivan et al. | |
| 5,265,595 A | 11/1993 | Rudolph | |
| 5,279,289 A | 1/1994 | Kirk | |
| 5,280,784 A | 1/1994 | Kohler | |
| 5,297,544 A * | 3/1994 | May et al. | 128/202.22 |
| 5,297,547 A | 3/1994 | Brain | |
| 5,311,862 A | 5/1994 | Blasdell et al. | |
| 5,322,057 A | 6/1994 | Raabe et al. | |
| 5,322,059 A * | 6/1994 | Walther | 128/205.23 |
| 5,323,774 A * | 6/1994 | Fehlauer | 128/206.12 |
| 5,343,878 A | 9/1994 | Scarberry et al. | |
| 5,349,949 A | 9/1994 | Schegerin | |
| 5,357,951 A | 10/1994 | Ratner | |
| 5,372,130 A | 12/1994 | Stern et al. | |
| 5,388,571 A | 2/1995 | Roberts et al. | |
| 5,404,871 A | 4/1995 | Goodman et al. | |
| 5,419,318 A | 5/1995 | Tayebi | |
| 5,429,126 A | 7/1995 | Bracken | |
| 5,429,683 A | 7/1995 | Le Mitouard | |
| 5,431,158 A | 7/1995 | Tirotta | |
| 5,438,981 A | 8/1995 | Starr et al. | |
| 5,441,046 A | 8/1995 | Starr et al. | |
| D362,061 S | 9/1995 | McGinnis et al. | |
| 5,477,852 A | 12/1995 | Landis et al. | |
| 5,479,920 A | 1/1996 | Piper et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,538,000 A | 7/1996 | Rudolph | |
| 5,540,223 A | 7/1996 | Starr et al. | |
| 5,542,128 A | 8/1996 | Lomas | |
| 5,546,936 A | 8/1996 | Virag et al. | |
| RE35,339 E | 10/1996 | Rapoport | |

(56) References Cited

U.S. PATENT DOCUMENTS

| | | | |
|---|---|---|---|
| 5,560,354 A | 10/1996 | Berthon-Jones et al. | |
| 5,570,682 A | 11/1996 | Johnson | |
| 5,570,689 A | 11/1996 | Starr et al. | |
| D377,089 S | 12/1996 | Starr et al. | |
| 5,592,938 A | 1/1997 | Scarberry et al. | |
| 5,608,647 A | 3/1997 | Rubsamen et al. | |
| 5,642,730 A | 7/1997 | Baran | |
| 5,647,355 A | 7/1997 | Starr et al. | |
| 5,647,357 A | 7/1997 | Barnett et al. | |
| 5,649,532 A | 7/1997 | Griffiths | |
| 5,649,533 A | 7/1997 | Oren | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A | 8/1997 | Landis et al. | |
| 5,660,174 A | 8/1997 | Jacobelli | |
| 5,662,101 A | 9/1997 | Ogden et al. | |
| 5,666,946 A | 9/1997 | Langenback | |
| 5,685,296 A | 11/1997 | Zdrojkowski et al. | |
| 5,687,715 A | 11/1997 | Landis et al. | |
| 5,715,814 A | 2/1998 | Ebers | |
| 5,724,965 A | 3/1998 | Handke et al. | |
| 5,746,201 A | 5/1998 | Kidd | |
| 5,813,423 A | 9/1998 | Kirchgeorg | |
| 5,832,918 A | 11/1998 | Pantino | |
| 5,884,624 A | 3/1999 | Barnett et al. | |
| 5,921,239 A | 7/1999 | McCall et al. | |
| 6,082,360 A | 7/2000 | Rudolph et al. | |
| 6,102,040 A | 8/2000 | Tayebi et al. | |
| 6,112,746 A * | 9/2000 | Kwok et al. | 128/207.13 |
| 6,119,693 A | 9/2000 | Kwok et al. | |
| 6,357,441 B1 | 3/2002 | Kwok et al. | |
| 6,412,487 B1 | 7/2002 | Gunaratnam et al. | |
| 6,513,526 B2 * | 2/2003 | Kwok et al. | 128/206.24 |
| 6,581,602 B2 | 6/2003 | Kwok et al. | |
| 6,634,358 B2 * | 10/2003 | Kwok et al. | 128/205.25 |
| 6,701,927 B2 * | 3/2004 | Kwok et al. | 128/207.13 |
| 6,871,649 B2 * | 3/2005 | Kwok et al. | 128/206.24 |
| 7,007,696 B2 | 3/2006 | Palkon et al. | |
| 7,069,933 B2 * | 7/2006 | Kwok et al. | 128/206.24 |
| 7,178,527 B2 * | 2/2007 | Kwok et al. | 128/207.13 |
| 2002/0074001 A1 | 6/2002 | Kwok et al. | |
| 2006/0201515 A1 * | 9/2006 | Kwok et al. | 128/206.24 |

FOREIGN PATENT DOCUMENTS

| | | |
|---|---|---|
| AU | 94/64816 B | 12/1994 |
| AU | 95/16178 B | 7/1995 |
| AU | 9459430 | 2/1996 |
| AU | A32914/95 | 2/1996 |
| AU | A 41018/97 | 4/1998 |
| AU | A 89312/98 | 1/1999 |
| CA | 1039144 | 9/1928 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | 195 48 380 A1 | 12/1994 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 | 7/1987 |
| EP | 0 264 772 | 10/1987 |
| EP | 0 303 090 | 7/1988 |
| EP | 0 386 605 A1 | 2/1990 |
| EP | 0 462 701 A1 | 5/1991 |
| EP | 0427474 A2 | 5/1991 |
| EP | 0549 299 A2 | 6/1993 |
| EP | 0 602 424 | 11/1993 |
| EP | 0 608 684 A1 | 8/1994 |
| EP | 0 634 186 A2 | 1/1995 |
| EP | 0 697 225 | 7/1995 |
| EP | 178 925 A2 | 4/1996 |
| EP | 0 747 078 A2 | 12/1996 |
| EP | 0 821 978 | 2/1998 |
| FR | 801629 | 8/1936 |
| FR | 858749 | 12/1940 |
| FR | 2 574 657 A1 | 6/1986 |
| FR | 2 658 725 A1 | 8/1991 |
| FR | 2 749 176 | 12/1997 |
| GB | 775911 | 5/1957 |
| GB | 1395391 | 5/1975 |
| GB | 1 467 828 | 3/1977 |
| GB | 2005547 | 4/1979 |
| GB | 2145335 A | 3/1985 |
| GB | 2147506 A | 5/1985 |
| GB | 2 164 569 A | 3/1986 |
| GB | 2211098 A | 6/1989 |
| GB | 2 267 648 A | 12/1993 |
| IT | 326983 | 6/1935 |
| JP | 44-16955 | 7/1969 |
| JP | 54-90892 | 7/1979 |
| JP | 09/216240 A | 8/1997 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/19055 | 9/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |

OTHER PUBLICATIONS

Office Action issued in related U.S. Appl. No. 11/826,267 (Oct. 7, 2010).

Notice of Opposition for corresponding European Application No. 06115004.1, dated Feb. 9, 2012, 27 pages.

"ResMed Sullivan Mirage—The Mirage is Real—A Perfect Fit—First Time," product brochure © ResMed Limited 1997, 4 pages.

Mirage Spare Parts Brochure, 1997, 2 pages.

Respironics, Inc. "Nasal Mask and Accessories Guide," Dec. 23, 1991, 6 pages.

"InterVENTions, A Ventilatory Care Newsletter," vol. 93, No. 1, Mar. 1993, Respironics. Inc., 16 pages.

"Order" from *Respironics. Inc.* v. *ResCare Limited* et al. case, Civil Action No. 95-151, with Exhibits E and G related to information allegedly available before Jul. 26, 1995, 20 pages.

Instructions for Use for the Comfort Flap Small Child Contour Nasal Mask Accessory, Respironics Inc., Jul. 19, 1993, 2 pages.

"Comfort Flap™ Improves the Seal on Reusable Contour Nasal Masks," InterVENTions. vol. 3, No. 1. Mar. 1993, 2 pages.

Mask 1 Photographs, Respironics Inc., Reusable Full Mask (small) Part #452033 Lot #951108.

Mask 2 Photographs. Puritan—Bennett, Adam Curcuit , Shell Part # 231700, Swivel Part # 616329-00, Pillows (medium) Part #616324.

Mask 3, Photographs, DeVilbiss Healthcare Inc., DeVilbiss Seal-Ring and CPAP Mask Kit (medium), Part 73510-669.

(56) References Cited

OTHER PUBLICATIONS

Mask 4 Photographs, Respironics Inc., Monarch Mini Mask with Pressure Port. Part # 572004, Monarch Headgear, Part # 572011.
Mask 5 Photographs, Healthdyne Technologies, Nasal CPAP Mask (medium narrow), Part # 702510.
Mask 6 Photographs. Healthdyne Technologies, Soft Series Nasal CPAP Mask, Part # 702020.
Mask 7 Photographs, DeVilbiss Healthcare Inc., Small Mask and Seal Rings, Part # 73510-668.
Mask 8 Photographs. Respironics Inc., Reusable Contour Mask (medium), Part # 302180.
Mask 9 Photographs, Healthdyne Technologies, Healthdyne Large Headgear.
Mask 10 Photographs, Respironics Inc., Soft Cap (medium), Part # 302142.
Mask 11 Photographs, Weinmann: Hamburg, Nasalmaskensystem mit Schalldämpfer (medium), Part # WN 23105.
Mask 12 Photographs, Life Care.
Mask 13 Photographs, Healthdyne Technologies.
Mask 14 Photograph, King System.
Mask 15 Photographs, Respironics Inc., Paediatric Mask.
Mask 16 Photographs, Hans Rudolph Inc., Hans Rudolph Silicone Rubber Face Mask/8900.

* cited by examiner

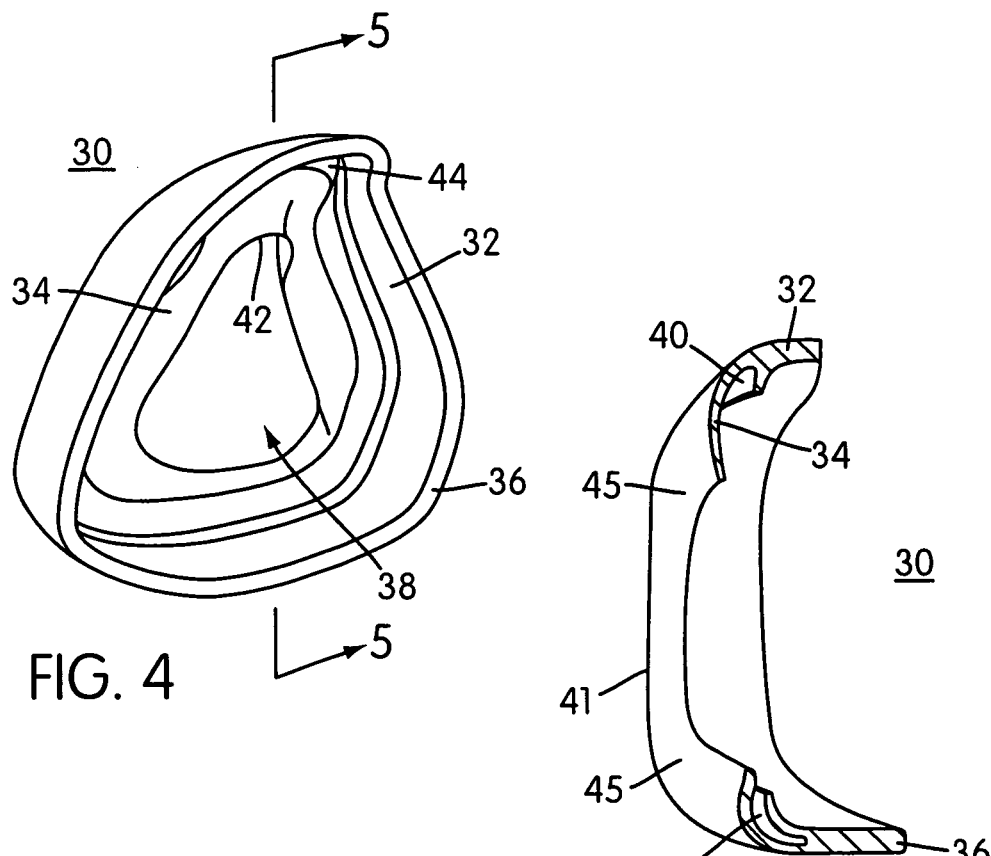
FIG. 4
FIG. 5
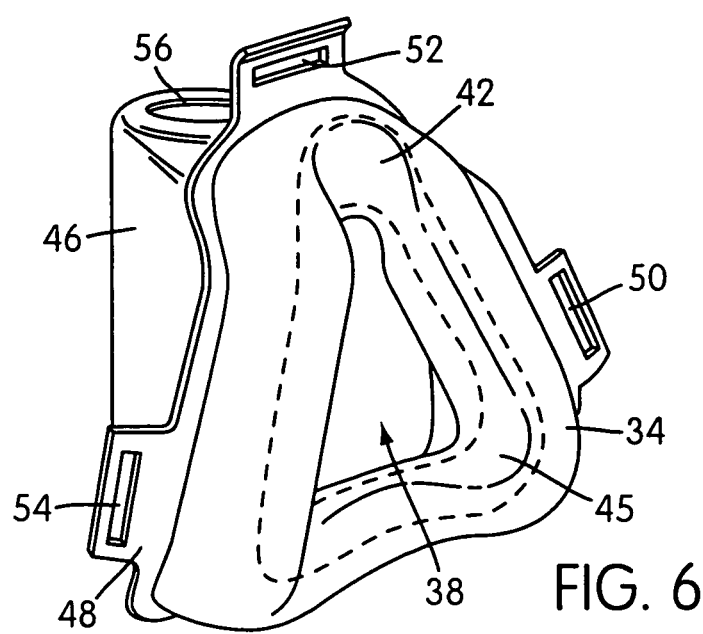
FIG. 6

MASK

CROSS REFERENCE TO RELATED APPLICATIONS

This application is a continuation of U.S. application Ser. No. 10/068,963, filed Feb. 11, 2002, allowed, which is a continuation of U.S. application Ser. No. 09/230,491, filed Aug. 11, 1999, now U.S. Pat. No. 6,357,441, which claims the benefit of Australian Patent Application No. P01265, filed Jul. 26, 1996, through PCT Application No. PCT/AU97/00450, filed Jul. 16, 1997 (published as WO 98/04310 on Feb. 5, 1998). This application contains subject matter related to U.S. application Ser. No. 08/791,212, filed Jan. 31, 1997, now U.S. Pat. No. 6,112,746, incorporated by reference in its entirety, which also claims priority to Australian Provisional Patent Application No. PO 1265, filed Jul. 26, 1996.

FIELD OF THE INVENTION

The invention relates generally to a nasal mask and to a cushion therefor, for example, for use in the treatment of respiratory conditions and in assisted respiration.

BACKGROUND OF THE INVENTION

Nasal masks are commonly used in the treatment of respiratory conditions and sleep disorders (e.g., obstructive sleep apnea) by delivering a flow of breathable gas for, or to assist patient respiration. These nasal masks typically receive a gas supply line which delivers gas into a chamber formed by walls of the mask. The walls usually are semi-rigid and have a face contacting portion including an aperture which is aligned with the wearer's nostrils. The face contacting portion can comprise a soft, resilient elastomeric material which may conform to various facial contours. The mask normally is secured to the wearer's head by straps. The straps are adjusted to pull the mask against the face with sufficient force to achieve a gas tight seal between the mask and the wearer's face. Gas is thus delivered to the mask and through the aperture to the wearer's nasal passages.

Problems often arise with masks of the above configuration. For example, the mask may be dislodged, thereby breaking the seal between the mask and wearer. This may occur if the wearer rolls over when sleeping thereby creating a drag force on the gas supply line which is transmitted to the mask, breaking the seal. In the case of a mask being used for the administration of Continuous Positive Airway Pressure (CPAP) treatment for the condition obstructive sleep apnea, such a leak can result in the pressure supplied to the entrance of the wearer's airway being below the therapeutic value, and the treatment becoming ineffective.

Another problem is that the face contacting portion may apply excessive pressure to the wearer's face resulting in discomfort and possibly skin irritation. This excessive forces. In some cases these excessive pressures and forces may cause the face to distort to conform with the face contacting portion to increase wearer discomfort, facial soreness and ulceration.

Other types of devices exist whereby small nostril nosepieces (pillows) are held in place by a harness strapped over the wearer's head, for example as shown in prior art U.S. Pat. No. 4,782,832. While this arrangement may alleviate some problems regarding seal breakage and skin abrasion, the harnesses associated with such devices are quite cumbersome for the wearer, as are the gas supply lines. Also, air 'jetting' into the nostrils can be irritating to the patient making such devices generally uncomfortable to use.

In FIGS. 1-3, a prior art nasal cushion 10. generally equivalent to that shown in prior art U.S. Pat. No. 5,243,971, is first described.

As shown, the cushion 10 generally includes a base 11 from which depends a semi-rigid cushion frame 12 formed of elastomeric material. Attached over the outside of the frame 12 is a membrane 15, also of elastomeric material, having at its distal end a face contacting portion 14. The frame 12 and the membrane 15 generally form a chamber 17 into which the wearer's nose can be received. The frame 12 has a notch 19 to accommodate the bridge of the wearer's nose. The base 11 includes slots 13 to accommodate straps (not shown) to secure the cushion 10 and a mask body (not shown) in combination to the wearer's head.

An aperture 16 is formed at the end of the membrane 15 distal from the frame 12 providing access for a wearer's nose 20 to the chamber 17 as noted. As shown, the aperture 16 in an unflexed state is generally circular (or elliptical) and is large enough to allow partial entry of the wearer's nose. The resilience of the membrane material allows the face contacting portion 14 and the aperture 16 to invert when the nose is received. The inverted membrane arrangement relies upon a positive pressure of supplied gas within the mask to effect a seal to the wearer's face. The seal is characterised as a "rolling edge seal", in that there can be motion of the cushion 10 relative to the patient's face yet the seal is maintained. Even so, a tuck 22 arises in the vicinity of the upper lip due to the circular shape of the aperture, and it is from this tuck that leaks can arise due to head and body movement during sleep.

It is an object of the invention to overcome or at least substantially ameliorate one or more of the foregoing disadvantages.

SUMMARY OF THE INVENTION

In one broad form, the invention discloses a nasal mask cushion to sealingly connect a mask to a wearer's face, the cushion comprising:

a substantially triangularly-shaped frame of resilient material having a rim to surround the wearer's nose;

a membrane also of resilient material, the membrane being relatively more flexible than the frame, and being of the same general shape as said rim and fixed to and extending away from the frame so as to have an outer surface spaced from the rim, a portion of said outer surface forming a face contacting seal; and a nose-receiving cavity bounded by said frame and said membrane;

and wherein said seal portion is generally coterminous with respect to said rim and is resiliently deformable towards the rim in use of the cushion.

Preferably, the rim and seal portion are shaped to generally match facial contours of the facial tissue around the sides and over the bridge of the nose and between the base of the nose and the top lip.

In one particularly advantageous form, the membrane is substantially saddle-shaped. The membrane further has a centrally located aperture through which the wearer's nose passes to enter said cavity.

It is preferred that the cushion and membrane each include a co-located notch to accommodate the bridge of the nose of the wearer. Typically, the seal portion contacts at least the wearer's nose, and preferably, also the facial tissue around the sides and over the bridge of the nose and between the base of the nose and the top lip.

The invention further discloses a nasal mask for connection to a wearer's face comprising:

a mask body for connection with a supply of breathable gas; and a nasal cushion, the body and cushion defining a nose-receiving cavity, the cushion including:

a substantially triangularly-shaped frame of resilient material having a rim to surround the wearer's nose;

a membrane also of resilient material, the membrane being relatively more flexible than the frame, and being of the same general shape as said rim and fixed to and extending away from the frame-so as to have an outer surface spaced from the frame, a portion of said outer surface forming a face contacting seal;

and wherein said seal portion is generally coterminous with respect to said rim and is resiliently deformable towards the rim in use of the mask.

The mask body can further include attachment points from which securing straps can be attached, and by which the mask can be secured to the wearer's head. The nasal mask can yet further comprise an arm depending from said body from which a further securing strap(s) can be attached.

The invention further discloses nasal CPAP treatment apparatus comprising a flow generator for the supply of gas at a pressure elevated above atmospheric pressure to a gas delivery conduit, the conduit in turn coupled to a nasal mask as described immediately above.

In one particularly preferred form, a supply of gas can be provided to said cavity, said supply of gas assisting, but not solely causing maintenance of a seal by said seal forming portion of said membrane to the face of the wearer in use of the cushion.

Advantageously, because the membrane and the rim are substantially shaped to the facial contour, and the membrane does not need to turn in on itself, as in the prior art, thus contacting the face without folds or creases. With the cushion/mask secured to the wearer's head, the headstraps need only to be tensioned to balance the force due to mask gas pressure that tends to lift the mask off the face. Such relatively lower mask-to-face pressure results in greater patient comfort, and a reduction in the likelihood of skin irritation.

BRIEF DESCRIPTION OF THE DRAWINGS

An embodiment of the invention will now be described with reference to the accompanying drawings, in which:

FIG. 4 is a rear perspective view of a mask cushion embodying the present invention;

FIG. 5 is a cross-sectional view along line 5-5;

FIG. 6 is a perspective view of a nasal mask including the cushion of FIGS. 4 and 5.

DESCRIPTION OF THE PREFERRED EMBODIMENTS

Figure 1:
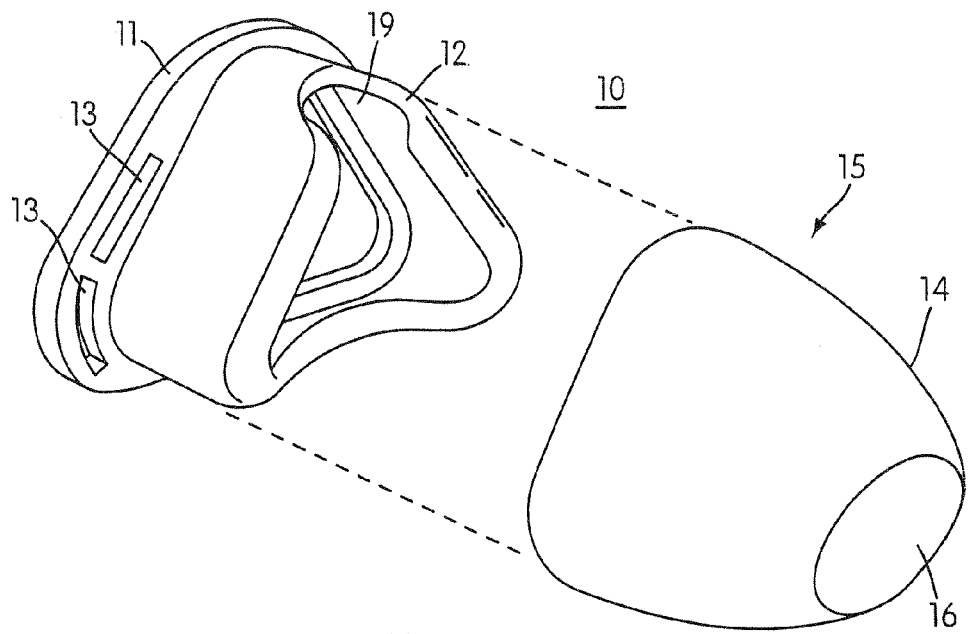
FIG. 1 is an exploded perspective view of a prior art nasal mask.

FIG. 4 shows a perspective view of a nasal cushion 30 embodying the invention. FIG. 5 shows the cross-sectional view along line 5-5. The cushion 30 comprises a substantially triangularly shaped frame 32 from which extends a rim 40 (otherwise referred to as a first membrane, a first molded layer or an interior layer, with the first membrane having a first rim) and a membrane 34 (otherwise referred to as a second membrane, a second molded layer or an exterior layer, with the second membrane having a second rim). The frame 32 has a scalloped edge 36 by which the cushion 30 is affixed to a mask body, as presently will be described.

The membrane 34 has an aperture 38 into which the wearer's nose is received in use of the cushion 30. The membrane 34 is spaced away a distance from the rim 40 of the frame 32, and its outer surface 41 is of substantially the same shape as the rim 40. The outer surface 41 of the membrane 34 and the rim 40 of the frame 32 also can be described as generally saddle shaped. The shaping of the outer surface 41 of the membrane 34 and the rim 40 of the frame 32 also include respective notches 42, 44 that receive the bridge of the wearer's nose in use of the cushion 30.

As is best seen in FIG. 5, the frame 32 and the membrane 34 are integrally formed, typically by in a one-shot molding process. The frame 32 and the membrane 34 are fabricated from a resilient material. One suitable such material is Silastic™ silicone elastomer manufactured by Dow Corning. The frame 32, in one preferred embodiment, has a typical thickness at its rim 40 of 1.5 mm. The membrane 34, in a preferred embodiment, has a typical thickness of 0.35 mm. In this way, the membrane 34 is relatively more flexible than the rim 40.

In use of the cushion 30, a wearer's nose will be inserted in the aperture 38 to engage a seal forming portion 45 (formed between the dashed lines) of the outer surface 41 to cause deformation of the membrane 34. Depending upon the securing force supplied to the membrane 34, it may deform to appoint where it butts against the rim 40 of the frame 32. The frame 32 has a rigidity. sufficient to withstand usual securing pressures in use of the cushion 30 to tend to retain its shape and resist deformation. It thus acts as a supporting structure.

Referring now to FIG. 6, the nasal cushion 30 is shown attached to a mask body 46 by the edge 36 of the frame 32, adhered or otherwise secured to a flange 48 of the mask body 46. Only the outer surface 41 of the membrane 34 can be seen. The flange 48 includes three slots 50, 52 and 54 from which tensioning straps can be attached to secure the cushion 30 and the mask body 46 (in combination) to the head of a wearer.

The mask body 46 forms a cavity that can receive the nose of the wearer by the aperture 38. A port 56 is provided at the top of the mask body 46 by which breathable gas can be supplied to the chamber.

Figure 7:
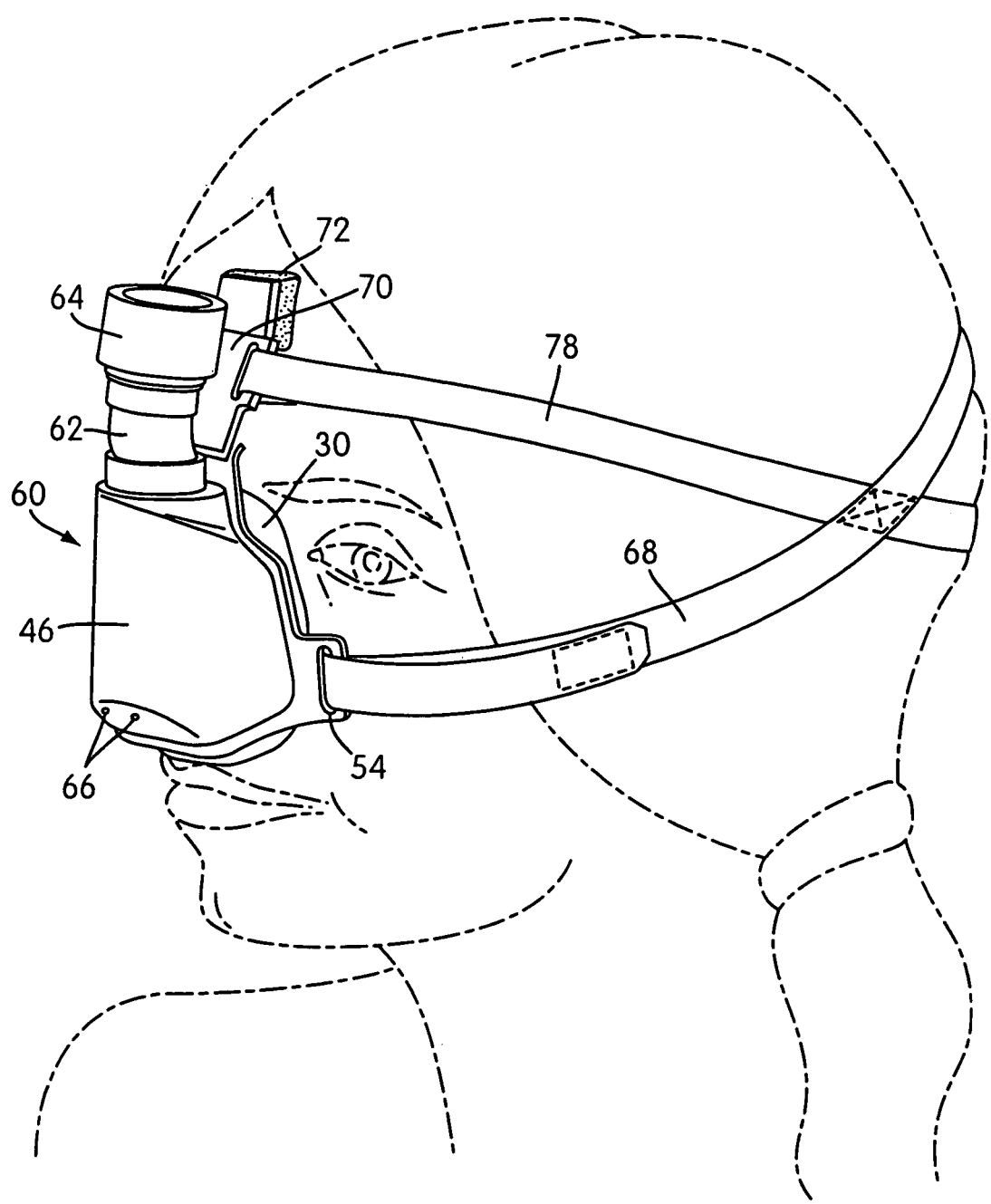
FIG. 7 is a perspective view of the nasal mask of FIG. 6 secured to a wearer's head.

Referring now to FIG. 7, there is shown a nasal mask 60 including the mask body 46 and the mask cushion 30. A coupling tube 62 is connected at one end with the inlet port 56, and at the other to a socket 64 into which can be received a gas delivery tube (not shown) for the supply of breathable gas to the chamber internal of the mask body 46. The mask body 46 also has two vent openings 66 by which expired gas is exhausted. A first fastening strap 68 is fixed between to the lower two slots 50,54. The upper slot 52 receives an arm 70, the top end of which has a resilient pad 72 to engage the forehead of the wearer. The arm 70 has two slots 74,76 along its side edges, by which a second fastening strap 78 is secured.

Figure 2:
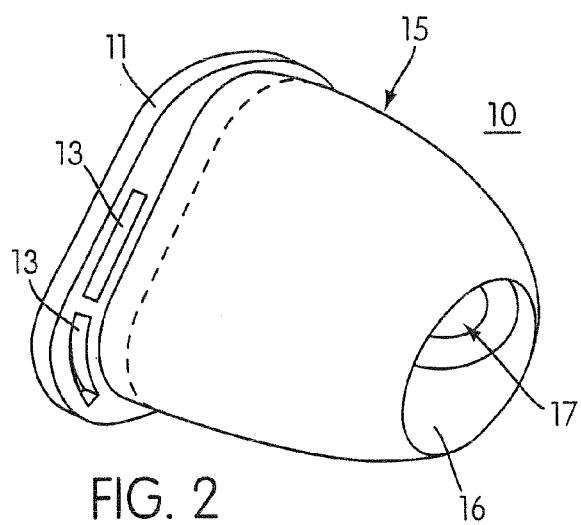
FIG. 2 is a perspective view of the prior art nasal mask of FIG. 1.
Figure 3:
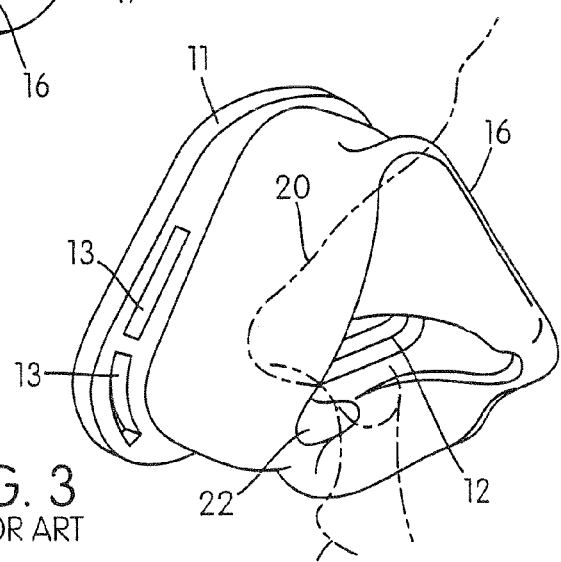
FIG. 3 is a perspective view of the prior art nasal mask attached to a wearer.

In fitting the nasal mask 60, the wearer's nose is received through the aperture 38 into the chamber within the mask body 46. The seal forming portion 45 thus contacts both the surface of the wearer's nose and a portion of the wearer's face in the region between the base of the nose and the upper lip, and around the sides and over the bridge of the nose. The shape of the seal forming portion 45 is particularly suited to effectively seal the difficult region of the facial contour that is the crease between the sides of the nose and the face. Depending upon the tension applied by the fastening straps 68,78, a seal is formed with the membrane 34 remaining spaced from the rim 40 of the cushion frame 32. While the provision of pressurised gas to the chamber of the mask body 46 assists in the maintenance of a seal between the membrane 34 and the wearer's nose and face, it is not essential in most cases, and an effective seal will be formed absent any such pressurised gas. The seal formed between the membrane 34 and the wearer's nose and face is not in the nature of a rolling seal in the manner of prior art as shown in FIGS. 1 to 3, as on relative movement of the mask 60 in relation to the wearer's head, the nose will be restrained by contacting the frame 32. Thus only limited relative motion between the mask 60 and the wearer's nose and face occurs.

The membrane 34 closely imitates the facial contour, and because of its relatively lesser stiffness than the frame 32, can conform to particular facial structures with minimum force, and without a tendency to fold or crease.

If the fastening strap 68,78 are tensioned to excess, the membrane 34 deforms to abut the rim 40 of the cushion 32, the frame 32 thus acting as an "end limit". In such a configuration, almost zero relative movement can occur between the mask 60 and the wearer's head.

The nasal cushion 30 and nasal mask 60 has been described with reference to CPAP or assisted respiration treatment, however it is to be understood that the invention generally is applicable to any application where gas and/or atomised liquid is to be supplied to the entrance of the nasal airways. Such applications include nebulisers, gas masks and anaesthetic machines.

The invention claimed is:

1. A mask comprising:
a mask body for connection with a supply of breathable gas; and
a compliant patient interface defining at least a portion of a breathing chamber, said interface including
a frame, said frame being of resilient material and having a first membrane, the first membrane including a first molded rim disposed within the breathing chamber and extending along at least a portion of an inner perimeter of the frame, said frame having a front portion with an edge structured to be coupled to the mask body; and
a second membrane of resilient material, said second membrane having a second molded rim, said second membrane rim spaced an open distance from said first membrane rim along an entire length of the second membrane when the mask is not in use, a portion of said second membrane rim forming a face contacting seal, wherein the substantially full perimeter of the second molded rim is provided in covering yet spaced relation to the first molded rim,
wherein along at least a portion of the perimeter of the second membrane, a surface of the second membrane is deformable from said spaced distance to abut against and contact a surface of the first membrane in dependence at least in part on a deformation force applied to the second membrane, and
wherein the first and second membranes are formed as a one-piece unit.

2. The mask according to claim 1, wherein said distance is greater than a thickness of the first molded rim, said distance measured when the mask is not in use.

3. The mask of claim 1, wherein the second membrane is conformable, in use, to various facial structures that contribute to the deformation force applied to the second membrane.

4. The mask of claim 3, wherein a first deformation position of the second membrane is defined by the first membrane.

5. The mask of claim 4, wherein the first deformation position is not reached depending on the deformation force.

6. The mask of claim 1, wherein the first membrane is thicker than the second membrane.

7. The mask of claim 6, wherein the first membrane is about four times as thick as the second membrane.

8. The mask of claim 1, wherein the first and second membranes have substantially the same shape.

9. The mask according to claim 1, wherein the face contacting seal is provided only to the second membrane, while the first membrane includes no face contacting seal.

10. The mask according to claim 1, wherein the mask further comprises at least one headgear strap, and the deformation force depends at least in part on strap tension applied to the strap.

11. The mask of claim 1, wherein the first and second membranes are spaced from one another and do not contact one another when the mask is not in use.

12. The mask of claim 1, wherein an outer surface of the second molded rim is of substantially the same shape as the first molded rim,
wherein the second molded rim and face contacting seal portion are shaped to generally match facial contours of the facial tissue around the sides and over the bridge of the nose and between the base of the nose and the top lip; and
further wherein the shaping of the outer surface of the second membrane and the first molded rim of the frame include respective notches that receive the bridge of the wearer's nose in use of the mask.

13. A mask comprising:
a mask body for connection with a supply of breathable gas; and
a compliant interface defining at least a portion of a breathing chamber, said interface having a front portion with an edge structured to be coupled to the mask body, said interface including
a first membrane made of resilient material, the first membrane including a first molded layer disposed within the breathing chamber; and
a second membrane of resilient material, said second membrane having a second molded layer, said second molded layer spaced an open distance from said first molded layer along an entire length of the second molded layer when the mask is not in use, a portion of said second membrane layer forming a face contacting seal, wherein the substantially full perimeter of the second molded layer is provided in covering yet spaced relation to the first molded layer,
wherein along at least a portion of the perimeter of the second membrane, a surface of the second membrane is deformable from said spaced distance to abut against and contact a surface of the first membrane in dependence at least in part on a deformation force applied to the second membrane, and
wherein the first and second membranes are formed as a one-piece unit.

14. The mask according to claim 13, wherein said distance is greater than a thickness of the first molded layer, said distance measured when the mask is not in use.

15. The mask of claim 13, wherein the second membrane is conformable, in use, to various facial structures that contribute to the deformation forces applied to the second membrane.

16. The mask of claim 15, wherein a first deformation position of the second membrane is defined by the first membrane.

17. The mask of claim 16, wherein the first deformation position is not reached depending on the deformation force.

18. The mask of claim 13, wherein the first membrane is thicker than the second membrane.

19. The mask of claim 13, wherein the first and second layers have substantially the same shape.

20. The mask of claim 13, wherein the mask body includes at least one vent opening.

21. The mask of claim 13, further comprising headgear and the mask body includes one or more structures to fasten a headgear strap.

22. The mask according to claim 13, wherein the face contacting seal is provided only to the second membrane, while the first membrane includes no face contacting seal.

23. The mask according to claim 13, wherein the mask further comprises at least one headgear strap, and the deformation force depends at least in part on strap tension applied to the strap.

24. The mask according to claim 13, wherein the first and second membranes are spaced from one another and do not contact one another when the mask is not in use.

25. The mask of claim 13, wherein an outer surface of the second molded layer is of substantially the same shape as the first molded layer, wherein the second molded layer and face contacting seal portion are shaped to generally match facial contours of the facial tissue around the sides and over the bridge of the nose and between the base of the nose and the top lip; and further wherein the shaping of an outer surface of the second membrane and the first molded layer include respective notches that receive the bridge of the wearer's nose in use of the mask.

26. A mask for use with the administration of CPAP therapy, comprising:

a mask body for connection with a supply of breathable gas pressurized above ambient; and a compliant patient contacting element including a multi-layered cushioning interface, said interface comprising an interior layer and an exterior layer having an entire length provided in spaced relation to the interior layer when the mask is not in use, said exterior layer being elastically and resiliently movable towards and away the interior layer in use, only said exterior layer forming a contacting seal with the patient in use, wherein along at least a portion of the perimeter of the exterior layer, a surface of the exterior layer is deformable from said spaced relation to abut against and contact against a surface of the interior layer in dependence at least in part on a deformation force applied to the exterior layer, and wherein the interior and exterior layers are formed as a one piece unit.

27. The mask according to claim 26, wherein said exterior layer is preformed to match the general shape of a portion of the patient's face in use.

28. The mask according to claim 26, wherein the mask further comprises at least one headgear strap, and the deformation force depends at least in part on strap tension applied to the strap.

29. The mask of claim 26, wherein the first and second layers are spaced from one another and do not contact one another when the mask is not in use.

30. The mask of claim 26, wherein the interior layer is of substantially the same shape as the exterior layer.

* * * * *